(12) United States Patent
Rocque et al.

(10) Patent No.: US 10,410,062 B2
(45) Date of Patent: Sep. 10, 2019

(54) SYSTEMS AND METHODS FOR OCCUPANCY MONITORING

(71) Applicant: KONINKLIJKE PHILIPS N.V., Eindhoven (NL)

(72) Inventors: Mukul Julius Rocque, Eindhoven (NL); Ihor Olehovych Kirenko, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 181 days.

(21) Appl. No.: 15/221,925

(22) Filed: Jul. 28, 2016

(65) Prior Publication Data
US 2017/0046577 A1 Feb. 16, 2017

(30) Foreign Application Priority Data

Aug. 10, 2015 (EP) .................................. 15180329

(51) Int. Cl.
*A61B 5/11* (2006.01)
*G06K 9/00* (2006.01)
(Continued)

(52) U.S. Cl.
CPC ........ *G06K 9/00771* (2013.01); *A61B 5/1115* (2013.01); *A61B 5/1128* (2013.01); *A61B 5/6891* (2013.01); *G01B 11/2513* (2013.01); *G01V 8/20* (2013.01); *G06K 9/00362* (2013.01); *G06K 9/2063* (2013.01); *H04N 5/23229* (2013.01)

(58) Field of Classification Search
CPC ........... G06K 9/00771; G06K 9/00362; G06K 9/2063; G01B 11/2513; G01V 8/20; H04N 5/23229; A61B 5/1115; A61B 5/1128
USPC ........................................................ 348/143
See application file for complete search history.

(56) References Cited

U.S. PATENT DOCUMENTS

| 7,431,700 B2 | 10/2008 | Aoki | |
|---|---|---|---|
| 2004/0046668 A1* | 3/2004 | Smith | A61B 5/1115 340/573.7 |

(Continued)

FOREIGN PATENT DOCUMENTS

| JP | 2002345766 | 12/2002 |
|---|---|---|
| JP | 2003032672 | 1/2003 |

(Continued)

OTHER PUBLICATIONS

Rigney, "Before the Fall", Technology Today, 2009.

*Primary Examiner* — Ayman A Abaza (57) ABSTRACT

An apparatus comprises a projector for fixed attachment to a moveable part of an item of furniture, which changes its position and/or orientation relative to a surface in response to a movement of a subject occupying the item of furniture. The projector is arranged to project a pattern onto the surface. At least one camera is arranged to capture sequential images of the surface. A processing unit is arranged to: receive the images from the at least one camera; detect the projected pattern in the received images; detect a change to at least one feature of the projected pattern in the received images; determine whether the detected change satisfies at least one predefined criterion for a subject exit event; and output a signal based on the determining.

19 Claims, 6 Drawing Sheets

(51) Int. Cl.
    *A61B 5/00*     (2006.01)
    *G06K 9/20*     (2006.01)
    *G01B 11/25*     (2006.01)
    *G01V 8/20*     (2006.01)
    *H04N 5/232*     (2006.01)

(56) References Cited

U.S. PATENT DOCUMENTS

| | | | |
|---|---|---|---|
| 2004/0141156 A1* | 7/2004 | Beardsley | G06K 9/2036 |
| | | | 353/69 |
| 2009/0245614 A1* | 10/2009 | Baldwin | G01B 11/245 |
| | | | 382/141 |
| 2009/0278934 A1 | 11/2009 | Ecker | |

FOREIGN PATENT DOCUMENTS

| | | |
|---|---|---|
| JP | 2006061222 | 3/2006 |
| WO | 2010/066824 | 6/2010 |
| WO | 2011/132118 | 10/2011 |
| WO | 2013/057648 | 4/2013 |
| WO | 2014208246 | 12/2014 |

\* cited by examiner

Fig. 8

SYSTEMS AND METHODS FOR OCCUPANCY MONITORING

CROSS REFERENCE TO RELATED APPLICATIONS

This application claims the benefit of European Patent Application Number 15180329.3 filed Aug. 10, 2015. This application is hereby incorporated by reference herein.

TECHNICAL FIELD OF THE INVENTION

The invention relates to an apparatus, system and method for monitoring a subject occupying an item of furniture, including detecting when a subject has exited an item of furniture.

BACKGROUND TO THE INVENTION

Detecting the movement and/or position of a subject is important in several healthcare applications. For example, it is often desired to prevent patients in hospital beds from moving in certain ways. As a result of medications, impaired memory, old age and/or other disabilities, patients who attempt to leave their beds without assistance often fall and injure themselves. Unassisted movement of a patient can also lead to medical devices attached to that patient becoming dislodged and ceasing to function properly.

However; the monitoring of patients who should not get out of bed without clinical assistance can place a significant burden on hospital staff.

Many current methods used for bed occupancy detection utilize a camera directed at the bed. In some examples a person (e.g. a medical professional) must constantly monitor the image feed from the camera. In other examples, such as the system described in US 2009/0278934, automated image analysis is used to detect bed exit events, but this requires complicated algorithms for detecting bed boundaries and classifying movements of the subject. Such algorithms can be confused by movements other than that of the subject (e.g. a blanket falling off the bed), leading to false alarms being raised when the subject is not attempting to exit the bed. Also, automated camera-based systems require recalibrating each time the relative position of the camera and the bed changes, and become unreliable if such recalibrations are not performed.

There is therefore a need for a system which can reliably monitor, with minimal input from medical staff, subjects occupying hospital beds and/or other items of furniture to detect when a subject attempts to leave a bed or other item of furniture.

SUMMARY OF THE INVENTION

According to a first aspect of the invention, there is provided an apparatus for monitoring a subject occupying an item of furniture. The apparatus comprises a projector for fixed attachment to a moveable part of an item of furniture. The moveable part is arranged to change its position and/or orientation relative to a surface in response to a movement of a subject occupying the item of furniture. The projector is arranged to project a pattern onto the surface. The apparatus further comprises at least one camera arranged to capture sequential images of the surface; and a processing unit. The processing unit is arranged to: receive the images from the at least one camera; detect the projected pattern in the received images; detect a change to at least one feature of the projected pattern in the received images; determine whether the detected change satisfies at least one predefined criterion for a subject exit event; and output a signal based on the determining.

In some embodiments the apparatus further comprises an additional projector for fixed attachment to a moveable part of an item of furniture, wherein the moveable part is arranged to change its position and/or orientation relative to a surface in response to a movement of a subject occupying the item of furniture, and wherein the additional projector is arranged to project a pattern onto the surface. In some such embodiments the projector and the additional projector are both for fixed attachment to the same moveable part of an item of furniture, and the projector is arranged to project onto a first region, and the additional projector is arranged to project onto a second region. In some such embodiments the at least one camera is arranged to capture sequential images, each of which includes the first region and the second region. In some embodiments the first region and the second region are located on opposite sides of the item of furniture.

In some embodiments the projector is for attachment to a first item of furniture and is arranged to project a first pattern onto a first region, and the additional projector is for attachment to a second item of furniture and is arranged to project a second pattern onto a second region. In some such embodiments the at least one camera is arranged to capture sequential images, each of which includes the first region and the second region. In some such embodiments the processing unit is arranged to: detect the first projected pattern and the second projected pattern in the received images, associate the first projected pattern with the first item of furniture and associate the second projected pattern with the second item of furniture; detect a change to at least one feature of the first projected pattern and detect a change to at least one feature of the second projected pattern, in the received images; determine whether the detected change to at least one feature of the first projected pattern satisfies at least one predefined criterion for a subject exit event and determine whether the detected change to at least one feature of the second projected pattern satisfies at least one predefined criterion for a subject exit event; and output a signal based on the determining, wherein the output signal contains information identifying the first item of furniture and/or the second item of furniture.

In some embodiments the projector is for attachment to an item of furniture at a first location, and the additional projector is for attachment to the same item of furniture at a second location, the second location being spatially separated from the first location. In some such embodiments the projector is arranged to project onto a first region and the additional projector is arranged to project onto a second region. In some embodiments the at least one camera is arranged to capture sequential images, each of which includes the first region and the second region. In some embodiments the second region is the same as the first region, and the projector is arranged to project a first partial pattern and the additional projector is arranged to project a second partial pattern such that a combined pattern comprising the first partial pattern and the second partial pattern is projected onto the first region. In some embodiments the processing unit is arranged to detect a change to at least one feature of the projected pattern by: detecting a first change associated with movement of the projector; detecting a second change associated with movement of the additional projector; and determining spatial information relating to a movement of a subject based on the detected first change and the detected second change.

In some embodiments the processing unit is arranged to detect a change to at least one feature of the projected pattern in the received images by: comparing a first image, acquired at a first time, to a second image, acquired at a second, later, time. In some such embodiments the comparing comprises: determining a first value relating to the at least one feature based on the first image; determining a second value relating to the at least one feature based on the second image; and calculating a change value for the at least one feature. In some embodiments the change value comprises the difference between the first determined value and the second determined value. In some embodiments the at least one predefined criterion comprises a minimum change value threshold. In some embodiments the processing unit is arranged to detect a change to at least one feature of the projected pattern in the received images by generating a change signal. In some embodiments the change signal is based on a time-series of calculated change values or on a time-series of determined first and/or second values. In some embodiments the at least one predefined criterion includes at least one condition relating to a feature of a change signal.

In some embodiments the at least one criterion comprises a predefined change signature corresponding to a movement type. In some such embodiments the processing unit is arranged to determine whether the detected change satisfies the least one predefined criterion for a subject exit event by determining whether the detected change matches the change signature.

In some embodiments the projector is arranged to project near-infrared light and the camera is arranged to detect near-infrared light.

There is also provided, according to a second aspect of the invention, a system for monitoring a subject occupying an item of furniture. The system comprises an item of furniture having a moveable part, wherein the moveable part is arranged to change its position and/or orientation relative to a surface in response to a movement of a subject occupying the item of furniture. The system further comprises a projector fixedly attached to the moveable part of the item of furniture, wherein the projector is arranged to project a pattern onto the surface. The system further comprises a camera arranged to capture sequential images of the surface; and a processing unit. The processing unit is arranged to: receive the images from the camera; detect the projected pattern in the received images, detect a change to at least one feature of the projected pattern in the received images; determine whether the detected change satisfies at least one predefined criterion for a subject exit event; and output a signal based on the determining.

In some embodiments the moveable part is associated with a side of the item of furniture opposite to a patient supporting side, such that the projector is located beneath a patient supporting surface of the item of furniture.

There is also provided, according to a third aspect of the invention, a method for monitoring a subject occupying an item of furniture. The method comprises:

receiving sequential images of a surface, each of the images including a pattern projected onto the surface by a projector fixedly attached to a moveable part of an item of furniture, wherein the moveable part is arranged to change its position and/or orientation relative to the surface in response to a movement of a subject occupying the item of furniture;

detecting the projected pattern in the received images, detecting a change to at least one feature of the projected pattern in the received images;

determining whether the detected change satisfies at least one predefined criterion for a subject exit event; and outputting a signal based on the determining.

Thus, embodiments of the invention advantageously provide a system which can reliably and unobtrusively monitor movements of a subject occupying an item of furniture, without requiring continual input from medical staff. In this manner bed (or other furniture) exit events can be detected automatically, which can considerably reduce the monitoring burden on medical staff. Moreover, the level of body motion of a subject in a bed can be continuously and unobtrusively monitored, without the need for sensors to be attached to the subject and without the involvement of medical staff. In this manner various physiological measures (such as sleep quality, leg restlessness) can be efficiently and conveniently monitored.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
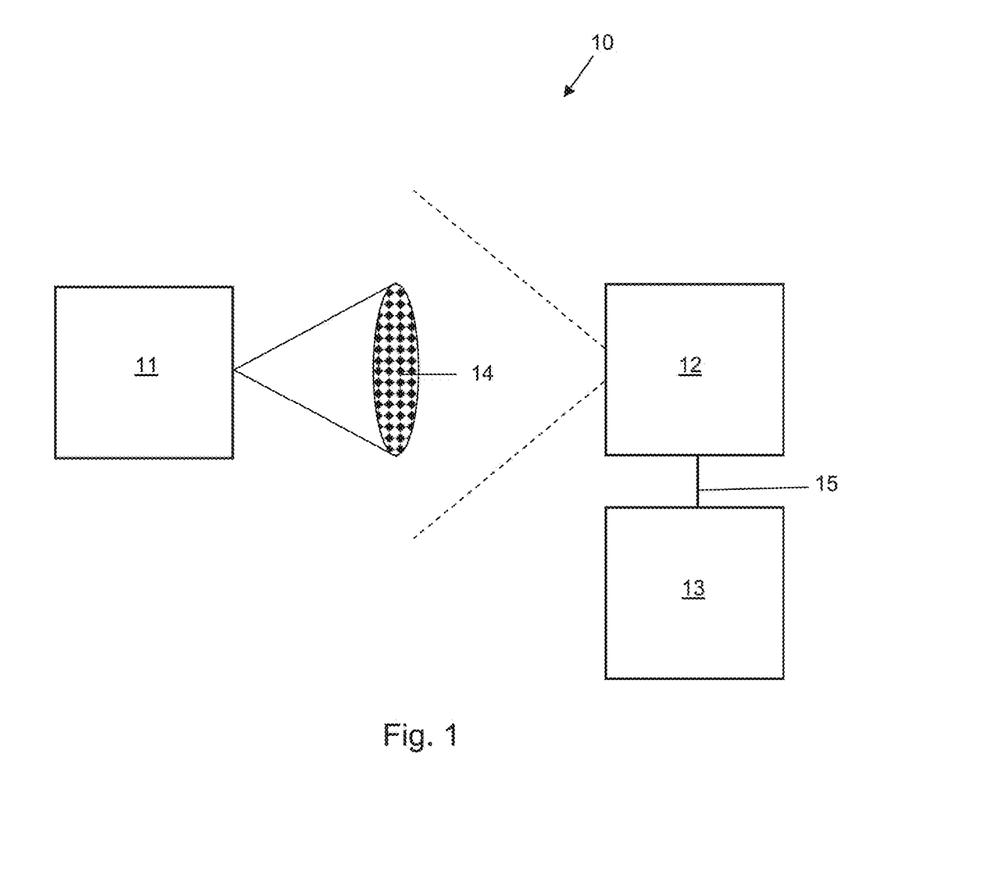
FIG. 1 is an illustration of an apparatus for detecting when a subject has exited an item of furniture, according to a general embodiment of the invention.

FIG. 1 shows an apparatus 10 for detecting when a subject has exited an item of furniture, according to a general embodiment. The apparatus comprises a projector 11, a camera 12, and a processing unit 13.

The phrase "processing unit" is used herein to refer to an entity or system for processing, for example, those that process in response to a signal or data and/or those that process autonomously. A processing unit should be understood to encompass microprocessors, microcontrollers, programmable digital signal processors, integrated circuits, computer software, computer hardware, electrical circuits, application specific integrated circuits, programmable logic devices, programmable gate arrays, programmable array logic, personal computers, chips, and any other combination of discrete analog, digital, or programmable components, or other devices capable of providing processing functions.

The projector 11 is configured for fixed attachment to a moveable part of an item of furniture (e.g. a flexible bed or chair base), wherein the moveable part is arranged to change its position and/or orientation relative to a surface (e.g. a floor on which the item of furniture is resting, or a wall near the item of furniture) in response to a movement of a subject occupying the item of furniture. In some embodiments the apparatus 10 comprises multiple projectors. In some such embodiments each of the multiple projectors can be arranged to project onto a different region of a surface on which the item of furniture is resting, or a different surface near to the item of furniture. In some embodiments each of the multiple projectors can be attached to a different item of furniture. In some embodiments each of the multiple projectors can be attached to a different moveable part of the same item of furniture.

The phrases "fixed attachment", "fixedly attached", and "fixed" are used herein to refer to a rigidly fixed attachment, for example such as which is commonly achieved by the use of hardware fasteners like screws or nuts and bolts.

The projector 11 is arranged to project a pattern 14 onto the surface. The projector 11 comprises an illumination source. In some embodiments the projector 11 is arranged such that substantially all of the light emitted by the projector has a wavelength in a predefined range. Preferably the projector 11 is arranged to emit light at a wavelength at which other light sources in the location where the apparatus is to be used do not emit a signification amount of light, or do not emit light at a high intensity relative to the intensity of light at that wavelength emitted by the light source 11. Advantageously, using a wavelength at which other light sources do not emit much light, or only emit with low intensity, ensures that the pattern will appear as a high-contrast object in images acquired by a camera arranged to preferentially detect light at that wavelength. In some such embodiments the projector 11 comprises an optical filter arranged to permit passage of light having a wavelength in the predefined range.

In some embodiments the illumination source emits near-infrared (IR) light. Advantageously, a projector which uses near-IR light to project the pattern 14 can prevent visual disturbance to the patient or hospital staff. In some embodiments the projector 11 is arranged such that the projected pattern amplifies movements of the moveable part of the item of furniture—in other words, such that a small movement of the moveable part (and thus of the projector) causes a larger change to the projected pattern 14. One way in which the degree of amplification of the projector movement can be altered is to alter the orientation of the projector (particularly the orientation of an illumination source of the projector) with respect to the surface. Shallower angles lead to higher amplification, as is shown by FIGS. 2a and 2b.

Figure 2A:
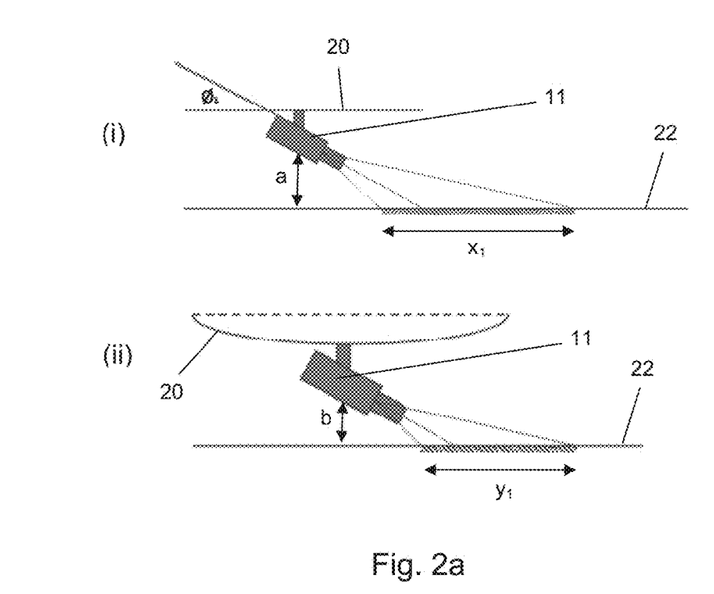
FIG. 2a shows a projector of the apparatus of FIG. 1, attached at a first angle to a flexible bed base.

FIG. 2a shows the projector 11 fixedly attached to a flexible bed base 20 at a first angle $\phi_1$ with respect to the part of the bed base 20 to which it is attached. The projector 11 is shown projecting a pattern onto a surface 22 (in this example the floor beneath the bed base 20). In FIG. 2a(i) the bed in which the bed base 20 is comprised is unoccupied, so that the flexible bed base is not deformed by the weight of a subject. Consequently, the projector 11 is at a first height, a, above the floor. At height a, the length of the pattern projected by the projector is a first length $x_1$. In FIG. 2a(ii) the bed is occupied by a subject, and the weight of the subject causes the flexible bed base 20 to deform towards the floor 22. Consequently, the projector 11 is at a second height, b, above the floor, which is less than the height a. At height b, the length of the projected pattern is a second length $y_1$. It can be seen by comparing parts (i) and (ii) of FIG. 2a that the pattern length $y_1$ is less than the pattern length $x_1$. Thus the pattern length decreases as the distance between the projector 11 and the floor 22 decreases. The pattern length therefore changes in response to movements of the flexible bed base 20 towards and away from the floor 22, and therefore in response to movements of a subject on the bed which cause such movements. Although FIG. 2a only shows the pattern length, it will be appreciated that, in the case of a 2-D pattern, the pattern width will also change in the same manner.

Figure 2B:
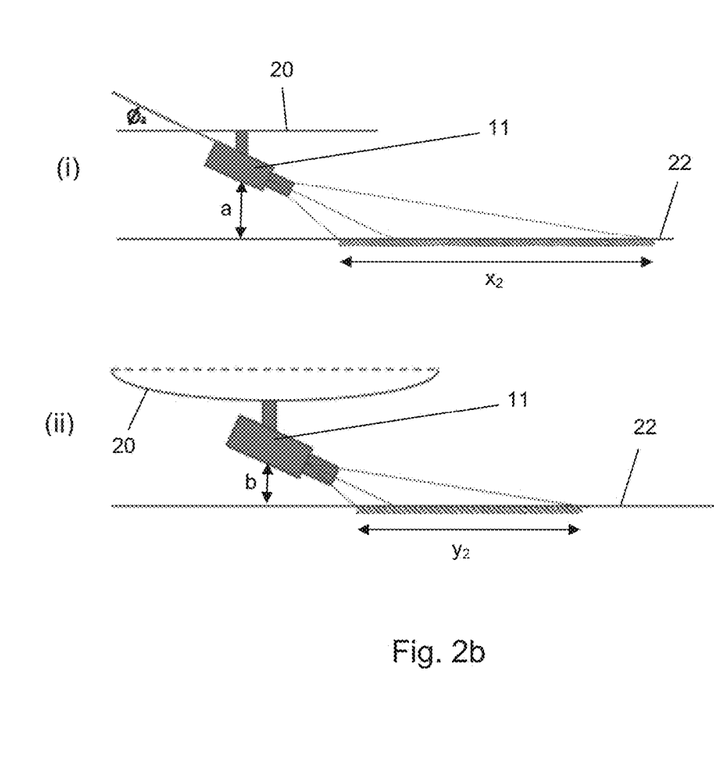
FIG. 2b shows the projector of FIG. 2a, attached at a second angle to the flexible bed base.

FIG. 2b shows the same arrangement as FIG. 2a, except that the projector 11 is fixed to the flexible bed base 20 at a second angle $\phi_2$ with respect to the part of the bed base 20 to which it is attached. The angle $\phi_2$ is less than the angle $\phi_1$. This difference in attachment angle has the effect that the light beams emitted by the projector 11 are incident on the floor 22 at a shallower angle as compared to the situation in FIG. 2a. Consequently, the length $x_2$ of the projected pattern when the bed is unoccupied is greater than the length $x_1$. The length $y_2$ of the projected pattern when the bed is occupied is also greater than the length $y_1$, but by a smaller amount. Consequently, the difference in pattern length between the occupied bed state and the unoccupied bed state is greater in FIG. 2b. Decreasing the angle $\phi$ yet further would further increase this length difference. The same will be true of the pattern width, in embodiments where a 2-D pattern is used. Thus, it can be seen that movements of the projector 11 towards and away from the surface 22 can be amplified in the projected pattern by reducing the angle between the projector 11 and the moveable part to which it is fixedly attached (in this example, the center of the flexible bed base 20).

In some embodiments in which the apparatus 10 comprises multiple projectors, each of the multiple projectors is fixedly attached to a different moveable part (or a different region of the same moveable part) of a single item of furniture, such that the multiple projectors are spatially separated. In some such embodiments each of the multiple projectors is arranged to project a pattern onto a different surface near to the item of furniture, or onto a different region of the same surface. In some embodiments each of the multiple projectors is arranged to project a pattern onto the same region of the surface, such that the resulting pattern is created by light from each of the multiple projectors. Advantageously, embodiments which utilize multiple spatially separated projectors can provide spatial information about movements of the subject on the item of furniture.

Figure 4A:
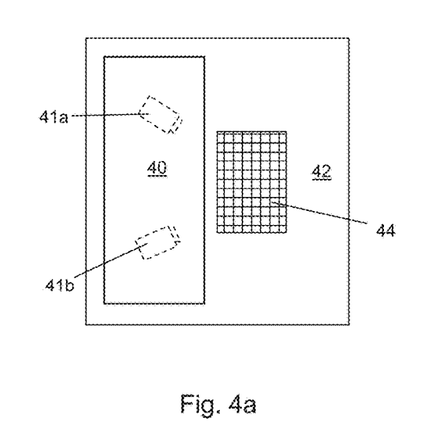
FIG. 4a shows a first example apparatus comprising multiple projectors according to an embodiment of the invention, in use with a bed.
Figure 4B:
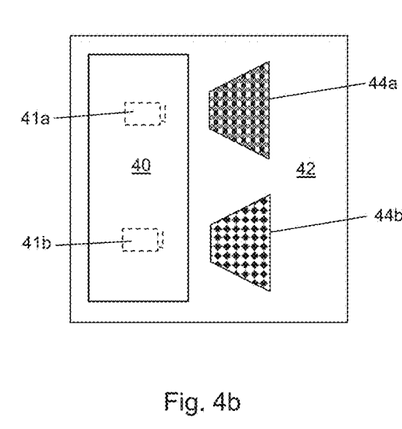
FIG. 4b shows a second example apparatus comprising multiple projectors according to an embodiment of the invention, in use with a bed.

For example, FIG. 4a shows one such embodiment in which a first projector 41a is fixed to a first area of a flexible bed base located beneath a top (head) end of a bed 40 and a second projector 41b is fixed to a second area of the flexible bed base located beneath the bottom (foot) end of the bed 40. In this example both projectors 41a, 41b are positioned to project onto the same region of the floor 42 on which the bed is resting. Movements of the first projector 41a result from movements of the head, arms or torso of a subject in the bed, whereas movements of the second projector 41b result from movement of the legs of a subject in the bed. In such embodiments the projected pattern 44 can be designed such that contributions to its deformation caused by movements from each of the first and second projectors can be distinguished by the processing unit 13, using appropriate algorithms. In an alternative configuration, shown in FIG. 4b, each of the projectors 41a, 41b is arranged to project onto a different region of the floor 42, and the processing unit 13 is arranged to detect two separate patterns 44a, 44b in each received image, and thereby to distinguish the movements of each projector 41a, 41b. The spatial information provided by the use of multiple projectors in this manner can enable various activity types (e.g. sitting, breathing, rolling over, restless leg movements, etc.) to be identified and distinguished between.

In some embodiments in which the apparatus 10 comprises multiple projectors, each of the multiple projectors is fixedly attached to the same moveable part or an adjacent moveable part of a single item of furniture. However; each of the multiple projectors is arranged to project onto a different region of a surface near the item of furniture, or a different surface near the item of furniture. The different surfaces or surface regions are located on different sides of the item of furniture. In some embodiments the different surfaces or surface regions are located on opposite sides of the item of furniture. Advantageously, embodiments which utilize multiple projectors to project patterns on different sides of the item of furniture can be very reliable, because obscuration of one of the projected patterns (e.g. by a pillow having been dropped onto the surface region onto which it is being projected) will not affect the operation or reliability of the apparatus 10.

Figure 5:
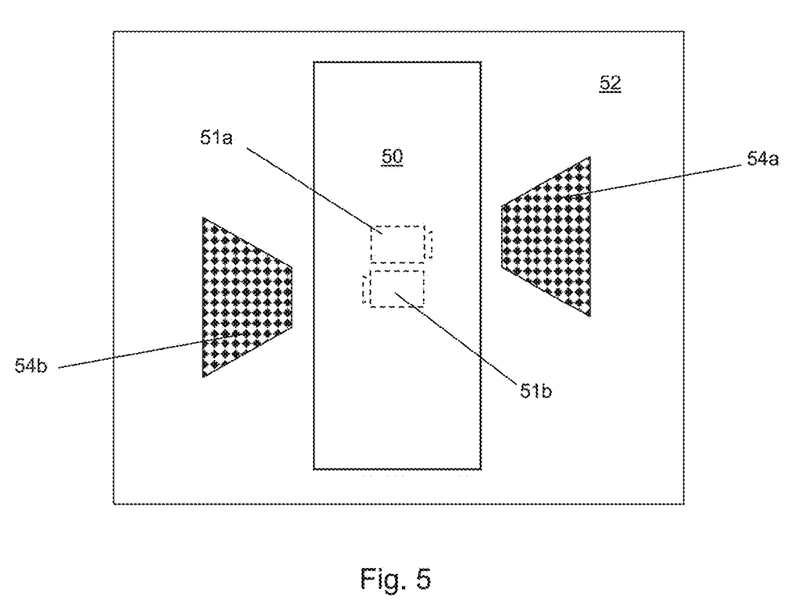
FIG. 5 shows a third example apparatus comprising multiple projectors according to an embodiment of the invention, in use with a bed.

For example, FIG. 5 shows one such embodiment in which a first projector 51a is fixed to a first area of a flexible bed base located centrally with respect to a bed 50, and a second projector 51b is also fixed to the first area, next to the first projector 51a, but positioned to project in the opposite direction to the first projector. The first projector 51a projects a pattern 54a onto the floor 52 adjacent a first long side of the bed 50, and the second projector 51b projects a pattern 54b (which in this example is the same as the pattern 54a projected by the first projector 51a) onto the floor 52 adjacent a second, opposite long side of the bed 50. Movements of the subject on the bed 50 cause both projectors 51a, 52a to move in an identical (or nearly identical) manner. In such embodiments the camera is positioned such that both projected patterns 54a, 54b are within its FOV, and the processing unit 13 is arranged to detect two patterns in the received images. When both patterns are detectable in the received images, in some embodiments the processing unit 13 is arranged to analyze both patterns and combine the results for use in making a final determination of whether the at least one criterion for a bed exit event has been satisfied. In other embodiments, when both patterns are visible the processing unit 13 is arranged to only analyze one of the patterns and to ignore the other pattern. When only one pattern is detectable in the received images (e.g. because one of the patterns is obscured for any reason), the processing unit detects changes and makes a determination of whether the at least one criterion for a bed exit event has been satisfied based only on the detectable pattern.

Figure 6A:
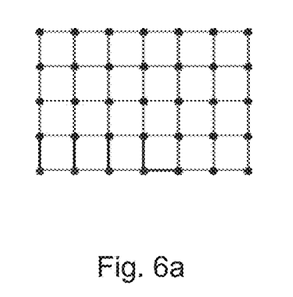
FIG. 6a is a first example pattern suitable for use in an embodiment of the invention.
Figure 6B:
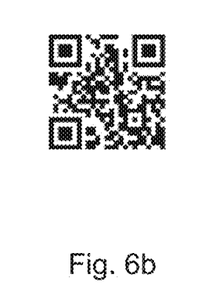
FIG. 6b is a second example pattern suitable for use in an embodiment of the invention.
Figure 6C:
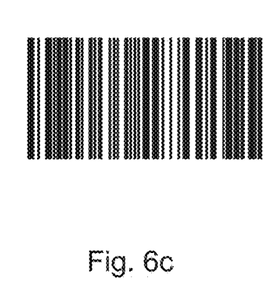
FIG. 6c is a third example pattern suitable for use in an embodiment of the invention.

The pattern 14 is preferably a well-defined pattern. In some embodiments the pattern is a 2-D pattern. The pattern 14 is arranged such that at least one feature of the pattern changes responsive to a change in the position and/or orientation of the projector 11 relative to the surface. The at least one feature which changes responsive to a change in the position and/or orientation of the projector may comprise one or more of: pattern length, pattern width, pattern diameter, pattern shape, distance between a first part of the pattern and a second part of the pattern (e.g. distance between a first grid node and a second grid node, if the pattern is a grid), total pattern area, etc. In some embodiments the pattern 14 is arranged to be easily segregated from the surrounding surface by an image processing algorithm. In some embodiments the pattern 14 comprises a grid. In some embodiments the pattern 14 comprises a barcode. In some embodiments the pattern 14 comprises a QR code. QR codes can be robustly detected with readily available algorithms, even in the face of varying illumination conditions and pattern orientations. In principle, any pattern the deformation of which is easily detectable could be used. FIGS. 6a-6c show some example patterns suitable to be employed by embodiments of the invention. FIGS. 6a, 6b and 6c show, respectively, a grid, a QR code and a barcode.

In some embodiments, e.g. embodiments in which the apparatus 10 comprises multiple projectors, the apparatus 10 may be arranged to project multiple patterns 14 onto one or more surfaces. In such embodiments each of the multiple patterns may be the same. Alternatively, at least some of the multiple patterns may differ from each other. In some embodiments each of the multiple patterns comprises a different barcode. In some embodiments each of the multiple patterns comprises a different QR code. In some embodiments a unique pattern is associated with each of multiple monitored items of furniture, and the pattern projected by any given projector is the pattern associated with the item of furniture to which that projector is attached. In some embodiments the projector 11 is arranged to selectively project one of multiple different patterns. Embodiments in which multiple projectors (i.e. each attached to a different item of furniture) each project a different pattern advantageously enable the automatic identification (e.g. by the processing unit 13) of each item of furniture being monitored by the apparatus 10.

Figure 7:
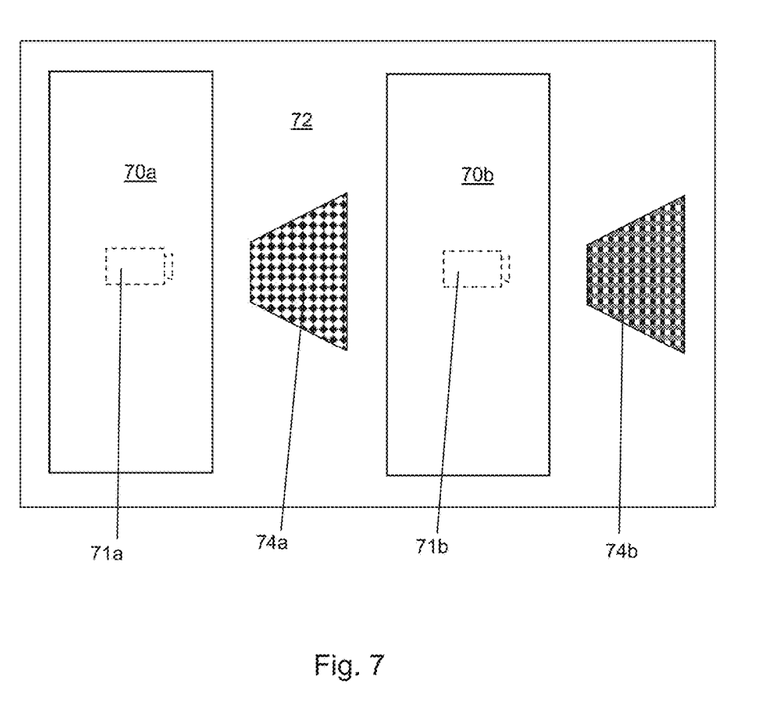
FIG. 7 shows a fourth example apparatus comprising multiple projectors according to an embodiment of the invention, in use with two beds.

For example, FIG. 7 shows one such embodiment in which a first projector 71a is fixed to a flexible bed base of a first bed 70a, and a second projector 71b is fixed to a flexible bed base of a second, different, bed 70b located adjacent the first bed. The first projector 71a projects a pattern 74a onto the floor 72 adjacent a long side of the first bed 70a, and the second projector 71b projects a different pattern 74b onto the floor 72 adjacent a long side of the second bed 70b. Movements of a subject on the first bed 70a cause the first projector 71a to move, and movements of a subject on the second bed 70b cause the second projector 71b to move. The camera is positioned such that both projected patterns 74a, 74b are within its FOV, and the processing unit 13 is arranged to detect two patterns in the received images. In some embodiments the processing unit 13 is arranged to analyze each pattern separately and simultaneously. In some embodiments the processing unit 13 is arranged to associate the first projected pattern with the first item of furniture and associate the second projected pattern with the second item of furniture, e.g. based on differences between the first pattern and the second pattern.

In some embodiments the projector 11 includes a user interface for receiving inputs from a user. In some such embodiments the user interface includes an on/off switch. In some embodiments the user interface includes a function to enable a user to select one of multiple possible patterns to be projected by the projector 11. In some embodiments the projector 11 is in communication with a remote processing unit, e.g. by means of a wired or wireless communications link. In some such embodiments the projector 11 is arranged to receive control signals from the remote processing unit. In some embodiments the remote processing unit is the processing unit 13 of the apparatus 10.

The camera 12 is arranged to capture sequential images of the surface. The camera 12 is arranged to detect light of the same type as the light emitted by the projector 11. In embodiments in which the projector 11 is arranged such that substantially all of the light emitted by the light source has a wavelength in a predefined range (e.g. by means of the projector comprising an optical filter), the least one camera is arranged to detect light having a wavelength in the predefined range. In some such embodiments the camera 12 comprises an optical filter arranged to permit the passage of light having a wavelength in the predefined range and to block the passage of light having a wavelength outside of the predefined range.

For example, in embodiments in which the projector 11 is arranged to emit near-IR light, the camera 12 is arranged to detect near-IR light and to generate images based on the detected near-IR light. In some embodiments the camera 12 is a 2-D camera. In some embodiments the camera 12 is a wide-angle camera. In some embodiments the apparatus 10 comprises a plurality of cameras, in which case the images from each camera may be stitched together by the processing unit 13, to create a single large image, before being analyzed to detect patterns etc. The camera 12 has a field of view (FOV), represented by the dashed lines in FIG. 1, which is preferably wide enough to encompass the projected pattern 14 when the projector 11 and the camera 12 are positioned for use.

The processing unit 13 is arranged to receive the images from the camera 12, e.g. via a communications link 15. The communications link 15 may be wired or wireless. The processing unit 13 is further arranged to detect the projected pattern 14 in the received images. The processing unit 13 may be arranged to use any suitable pattern detection algorithm(s) known in the art to detect the projected pattern 14. In some embodiments, e.g. embodiments in which the apparatus 10 comprises at least one camera 12 (e.g. arranged to view a relatively large area, such as a whole hospital ward) and multiple projectors 11 (e.g. attached to multiple items of furniture), the processing unit 13 is arranged to detect and distinguish between multiple projected patterns in the received images. In some such embodiments the processing unit 13 is arranged to associate each projected pattern detected in the received images with an item of furniture, e.g. based on rules linking items of furniture to patterns which are stored in a memory comprised in or connected to the processing unit 13. Advantageously, in such embodiments the apparatus 10 can monitor several items of furniture simultaneously. The processing unit 13 is further arranged to detect a change to at least one feature of the projected pattern 14 in the received images. The at least one feature can comprise one or more of: pattern length, pattern width, pattern diameter, pattern shape, distance between a first part of the pattern and a second part of the pattern, total pattern area. In embodiments in which the processing unit is arranged to detect multiple projected patterns, the processing unit is arranged to separately and simultaneously detect a change to at least one feature of the projected pattern in respect of each projected pattern detected in the received images.

In some embodiments the processing unit 13 is arranged to detect a change to at least one feature of the projected pattern 14 by comparing a first image, acquired at a first time, to a second image, acquired at a second, later, time. The second time may be immediately after the first time, or alternatively may be a predetermined length of time after the first time. In some such embodiments the processing unit 13 is arranged to determine a first value relating to the feature (e.g. a pattern length value) based on the first image, to determine a second value relating to the feature based on the second image, and to compare the two determined values. In some embodiments the processing unit is arranged to calculate a change value, which comprises the difference between the two determined values. In some such embodiments the processing unit 13 is arranged to determine that a change has occurred to the feature if the first and second determined values are not the same. In some embodiments the processing unit 13 is arranged to determine that a change has occurred to the feature if the first and second values differ by more than a predefined threshold (e.g. if a calculated change value is greater than the predefined threshold).

In some embodiments the processing unit 13 is arranged to generate a time-varying change signal for part or all of the time period covered by the received images. In some such embodiments the change signal comprises or is based on a time series of determined values relating to the feature. In some embodiments the change signal comprises or is based on a time series of change values relating to the feature. In some embodiments the processing unit 13 is arranged to determine values, calculate change values, and/or generate a change signal in respect of each of multiple features of the projected pattern 14.

The processing unit 13 is further arranged to determine whether the detected change satisfies at least one predefined criterion for a subject exit event. In some embodiments the predefined criterion comprises a set of one or more conditions. Conditions included in such a set can include one or more of: magnitude of the change, speed of the change, conditions relating to the shape of a change signal. Conditions relating to the shape of a change signal can comprise any or all of: a measure of the variability of a change signal, an amount of time for which the variability of a change signal exceeds a predefined threshold, frequency of periods when a change signal exceeds a predefined threshold, relative locations of peaks in a change signal, relative heights of peaks in a change signal, area under a change signal.

In some embodiments the processing unit 13 comprises or is in communication with a memory storing a set of change signatures corresponding to various different movement types (e.g. rolling over, sitting up, etc.). A change signature may comprise, e.g., a set of change values for a feature, a change signal for a feature, a combination of change values or change signals for multiple features, etc. In some such embodiments the at least one criterion comprises a change signature, and determining whether a detected change satisfies the at least one predefined criterion comprises determining whether the detected change matches the change signature. In some embodiments the processing unit 13 is further arranged to calculate confidence information in respect of each determination of whether the detected change satisfies at least one predefined criterion for a subject exit event.

The processing unit 13 is further arranged to output a signal based on the determining. In some embodiments the signal comprises a control signal, e.g. to a device having a wired or wireless communications link with the processing unit 13. Such a device could be, e.g., a communications device, a display device, an alarm device, etc. In such embodiments the control signal may be arranged, for example, to cause one or more of:

an alarm device (e.g. a visual or audio alarm generating device) to generate an alarm;

a communications device to generate a message to a caregiver;

a communications device to generate a message to the subject;

a communications device to send a signal to a remote device (e.g. a pager, PDA or mobile phone of a medical professional);

a display device (e.g. a monitor or screen) to display information.

In some embodiments the signal comprises a message to a caregiver, e.g. indicating that a bed exit event has been detected. In some embodiments the signal comprises a message to the subject, e.g., to instruct them to remain in bed until assistance arrives. In some embodiments the processing unit is arranged to output a plurality of signals, for example a communications signal to a communications device such as a mobile phone of a medical professional, and a control signal to an alarm device causing it to generate an alarm.

In some embodiments the processing unit 13 is further arranged to determine the orientation, with respect to the camera 12, of an item of furniture to which the projector is attached. Such a determination of orientation can be achieved, e.g., by analyzing the orientation of the projected pattern with respect to other features in the received images, or by means of a known automated or semi-automated techniques for predefining the orientation of the item of furniture in the image. In some such embodiments the processing unit 13 is further arranged to output a signal based on the determined orientation. In some such embodiments the signal based on the determined orientation contains orientation information, and is output to another camera-based monitoring system, e.g. which comprises a camera arranged to acquire images of the item of furniture. Advantageously, such embodiments can facilitate the automated calibration of camera-based monitoring systems other than the apparatus 10 which are arranged to acquire images of the item of furniture and/or a subject occupying the item of furniture, reducing or removing the need for medical personnel to recalibrate such systems when the item of furniture is moved.

In some embodiments (i.e. embodiments in which the apparatus 10 comprises multiple projectors for attachment to a single item of furniture) the processing unit 13 is arranged to detect contributions from each individual projector to detected changes. In some embodiments each of the multiple projectors is arranged to project onto a different surface, or a different region of the same surface. In such embodiments the processing unit 13 is arranged to detect a separate pattern for each projector, and to separately (but preferably simultaneously) detect changes to features of each of these patterns in the manner described above. In some embodiments the processing unit 13 is arranged to analyze detected changes in respect of all of the patterns together. In some embodiments each of the multiple projectors is arranged to project onto the same region of the same surface, such that a single overall pattern is created on that surface which comprises contributions from each of the multiple projectors. In such embodiments the processing unit 13 is arranged to analyze detected changes to the at least one feature of the detected pattern in order to distinguish contributions from each of the multiple projectors, to each detected change.

Analyzing the differences (e.g. in respect of angle, temporal behavior, etc.) between the changes to each of the multiple patterns, or to the contributions of each of the multiple projectors to an overall pattern, can enable spatial information about the body motion of a subject in a bed to be extracted. In some embodiments the processing unit 13 is arranged to determine a movement type (e.g. rolling over, sitting up, restless legs movements) based on such a combined analysis. For example, by analyzing differences in the degree of change of a feature two patterns, it can be determined whether the upper or lower part of a subject's torso is moving. In some such embodiments the processing unit is arranged to determine a movement type (e.g. rolling over, sitting up, restless legs movements) based on the analysis. In some such embodiments the at least one predefined criterion for a subject exit event comprises one or more conditions relating to movement type. For instance, a sitting-up position can serve as an early indication of a bed exit, so in some embodiments the at least one predefined criterion for a subject exit is defined such that a sitting up movement type must be identified (based on the detected changes) in order for the processor to determine that the predefined criterion is met.

Figure 3:
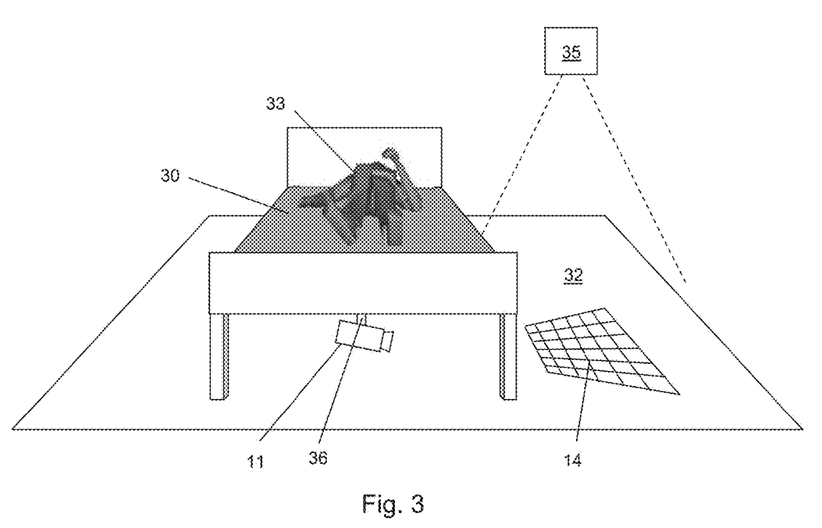
FIG. 3 shows the apparatus of FIG. 1 in use with a bed.

FIG. 3 shows the apparatus of FIG. 1 in use with an item of furniture. In the illustrated example the item of furniture comprises a hospital bed 30 having a flexible bed base (not visible) which moves up and down relative to the floor 32 on which the bed 30 is resting, responsive to movements of a subject 33 occupying the bed 30. However; in other examples the item of furniture can comprise another type of bed, a chair, a wheel chair, or any item of furniture having a moveable part which moves, relative to a surface onto which it is possible to project a pattern with the projector 11, in response to the movements of a subject occupying the item of furniture.

The moveable part can be any part of the item of furniture which moves towards and away from a surface on which the item of furniture is resting, responsive to movements of a subject occupying the item of furniture. Preferably the moveable part is associated with an underside of the item of furniture (i.e. a side opposite to a patient supporting side of the item of furniture), such that the projector 11, when attached to the moveable part, is located beneath a patient supporting surface of the item of furniture. Advantageously, locating the projector 11 beneath the patient supporting surface of the item of furniture means that it does not get in the way of subjects getting into or out of the item of furniture, or of medical staff working in the vicinity of the item of furniture (e.g. to care for a subject occupying the item of furniture). Additionally, the projected light beams are unlikely to become obscured during use of the apparatus 10 if the projector 11 is beneath the item of furniture 30.

In some examples the movement of the moveable part is caused by a change in the amount of the weight of the subject being supported by the moveable part. In some examples the moveable part to which the projector is attached comprises a component or region of a larger part, which is itself moveable responsive to movement of the subject. In some examples the moveable part comprises an elastic component (e.g. a spring, portion of elastic material, portion of rubber, etc.). In some examples the moveable part is connected to the rest of the item of furniture by an elastic component.

The projector 11 is fixedly attached to the flexible bed base, such that movements of the flexible bed base cause the projector 11 to experience movements of the same type and degree as the movements of the part of the flexible bed base to which the projector is attached. It is expected that the main component of the movements will be toward and away from the surface on which the bed is resting (i.e. the floor 32 in this example). However; if the subject changes position relative to the width of the bed, then (depending on the exact configuration of the bed base) it is possible that the angle of the part of the bed base to which the projector 11 is attached (and therefore the projector 11) relative to the floor 32 could change.

In some embodiments the projector 11 is directly attached to the moveable part. In some embodiments the projector 11 is indirectly attached to the moveable part, e.g. by means of an intermediate component such as a mounting bracket. In such embodiments the intermediate component is fixedly attached to the moveable part and the projector 11 is fixedly attached to the intermediate component. Use of an intermediate component such as a mounting bracket can increase the distance between the moveable part of the item of furniture 30 and/or permit a larger range of angles between the projector 11 and the moveable part. Advantageously, such an increased distance and/or angle range can avoid obscuration of the projected pattern, e.g. in cases where the item of furniture comprises protrusions which extend toward the surface on which it is resting. For example, many modern hospital beds are supported on complex mechanisms (e.g. for raising and lowering and/or changing the angle of the subject support surface), which comprise various such protrusions. When setting up the apparatus 10 with a particular item of furniture, decisions such as which moveable part to attach the projector 11 to, whether to use a mounting bracket, what angle to set the projector 11 at with respect to the moveable part, etc. will be taken (e.g. by an engineer installing the apparatus 10) based on the exact configuration of the particular item of furniture.

In the example of FIG. 3 the camera 12 and the processing unit 13 are integrated into a monitoring device 35. The projector 11 is fixedly attached to the flexible bed base, via a mounting bracket 36, so that it moves, together with the bed base, up and down relative to the floor 32 responsive to movements of the subject 33. The projector 11 is angled towards the floor 32 by an amount such that the pattern 14 is projected onto a section of the floor adjacent the bed 30.

When the subject 33 moves, e.g. sitting up to exit the bed, the flexible bed base moves up and down (relative to gravity) due to the weight of the subject being supported by different regions of the bed base as the movement progresses. Regions of the flexible bed base which support less of the subject's weight as the movement progresses will consequently move away from the floor 32. Regions of the flexible bed base which support more of the subject's weight as the movement progresses will consequently move toward the floor 32. The amount and direction of movement experienced by the part of the flexible bed base to which the projector 11 is attached (and therefore the projector 11) will depend on the location of the moveable part in relation to the subject's starting position on the item of furniture, and on the nature of the movement.

In the example of FIG. 3 the moveable part to which the projector is attached is located in the center of the bed base. When the patient is lying flat in the center of the bed, a first amount of the subject's weight will be supported by the part of the flexible bed base to which the projector 11 is attached, and the projector will be positioned at a first distance above the floor 32. If the subject sits straight up, more of the subject's weight will be supported by the part of the flexible bed base to which the projector 11 is attached, because the head end of the bed is no longer supporting any weight, and consequently the projector will be positioned closer to the floor (than the first position). By contrast, if the subject rolls to the side whilst still lying flat, less of the subject's weight will be supported by the part of the flexible bed base to which the projector 11 is attached, because the subject's body will no longer be directly over the part of the flexible bed base to which the projector is attached, and consequently the projector will be positioned further away from the floor (than the first position). Thus, different movement types will cause different patterns of changes to the height (and possibly also orientation) of the projector 11.

The movements of the projector 11 cause the size and/or shape of the projected pattern 14 to change. The nature of the change to the projected pattern depends on the nature of the movement. For example, movement of the projector 11 directly toward the floor 32 will cause a decrease in the length, width (and therefore area) of the pattern, as explained above in relation to FIGS. 2a and 2b. The distance between features within the pattern (e.g. grid nodes, if the pattern is a grid) will also decrease. An increase in the relative angle between the projector 11 and the floor 32 (which could occur, e.g., in the situation illustrated in FIGS. 2a(ii) and 2b(ii) if the projector was not located centrally with respect to the flexible bed base 20) will cause the position of the pattern on the floor 32 to shift closer to the edge of the bed 30. A decrease in the relative angle between the projector 11 and the floor 32 will cause the position of the pattern on the floor 32 to shift further from the edge of the bed 30. In practice, where changes of orientation of the projector are possible in addition to changes in height, any given movement of a subject will typically cause a combination of size changes and position changes to the projected pattern. The exact pattern of the changes depends on the nature of the movement, so it is possible to define characteristic pattern change signature for various common movement types (e.g. sitting up, rolling over, etc.).

In some embodiments the projector 11 is manually activated, e.g. by person activating an on-switch of the projector 11, and projects continually until it is manually deactivated, e.g. by a person activating an off-switch of the projector 11. In some embodiments the projector 11 is automatically activated, e.g. by a control signal from a processing unit. In some embodiments the projector 11 has a communications link with the processing unit 13 and is activated (and subsequently deactivated) by a control signal from the processing unit 13. Preferably the projector 11 is only activated during times when the item of furniture is in use. For the purposes of the invention, an item of furniture is considered to remain "in use" during temporary absences of a subject using the item of furniture, e.g. to visit the bathroom, or to undergo treatment. By contrast, an item of furniture is considered to be not in use during the period between the discharge of a subject who was previously occupying that item of furniture, and the first occupation of that item of furniture by a new subject.

The monitoring device 35 is positioned such that the field of view (FOV) of the camera 12, as represented by the dashed lines in FIG. 3, encompasses at least part of the projected pattern 14. Preferably the monitoring device 35 is positioned such that the support surface of the bed 30 is not within the FOV of the camera. This ensures that a subject occupying the bed will not be included in the images obtained by the camera. Not including the subject in the images is advantageous from a privacy point of view, and also to simplify the task of detecting and tracking pattern features in the captured images. However, embodiments are envisaged in which a single camera is used to monitor multiple projected patterns associated with multiple items of furniture, in which case the support surfaces of at least some of the monitored items of furniture will be within the FOV of the camera.

In use of the apparatus 10, the projector 11 is activated in one of the manners described above such that it continually projects the pattern 14 onto the surface 32. The camera 12 captures images of the surface 32, which include at least part of the projected pattern 14, during a recording period. In some embodiments the camera continually captures images during the whole time the apparatus 10 is in use, such that the recording period comprises the period for which the apparatus 10 is in use. In some embodiments the camera is activated in response to an event. In some such embodiments the event comprises a detection of motion of the subject by a separate motion detector (e.g. an accelerometer attached to the item of furniture, or a separate camera-based motion detection system). In some embodiments the camera is arranged to capture images for a predefined amount of time (i.e. the duration of the recording period is predefined). In some embodiments the captured images comprise video frames. In some embodiments the camera captures a series of still images.

Images captured by the camera are sent to the processing unit 13. The processing unit 13 continually assesses, on the basis of the captured images, whether a subject exit event is occurring (or has occurred), e.g. by performing the method shown in FIG. 8.

Figure 8:
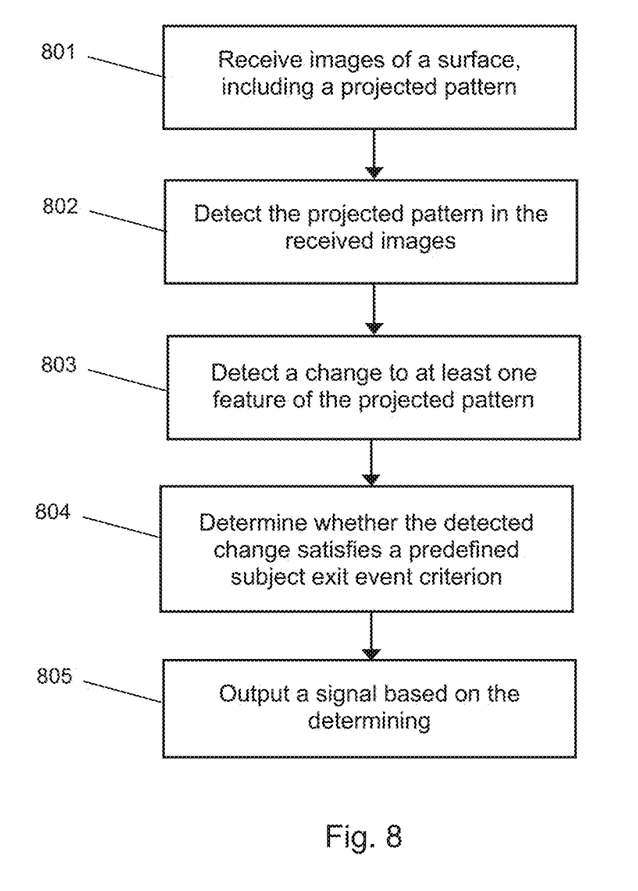
FIG. 8 is a flow chart illustrating a method for detecting when a subject has exited an item of furniture, according to a general embodiment of the invention.

FIG. 8 illustrates a method for detecting when a subject has exited an item of furniture. In a first step, 801, sequential images of a surface (e.g. the floor 32) are received (e.g. by the processing unit 13). Each of the images includes a pattern (e.g. the pattern 14) projected onto the surface by a projector (e.g. the projector 11, in any of the manners described above) which is fixedly attached to a moveable part of an item of furniture (e.g. the bed 30), the moveable part being arranged to change its position and/or orientation relative to the surface in response to a movement of a subject occupying the item of furniture (e.g. in any of the manners described above). In some embodiments the images are received from the camera which captured the images, e.g. via a wired or wireless communication link. In some embodiments the images are received from a remote server (e.g. a central hospital server), e.g. via a wired or wireless communication link. In some embodiments the images are received on a machine-readable non-transitory storage medium. In some embodiments the images are received in real time or near-real time (i.e. as they are captured by a camera). In some embodiments the images are received from multiple sources, e.g. a first camera, arranged to monitor a first item of furniture, and a second camera, arranged to monitor a second item of furniture.

In step 802 the projected pattern 14 is detected in the received images, e.g. by the processing unit 13. In some embodiments the projected pattern is detected in the manner described above in relation to the operation of the processing unit 13. In some embodiments performing step 802 comprises detecting the projected pattern 14 in each frame of a received video stream. In some embodiments performing step 802 comprises detecting the projected pattern 14 in each image of a received series of still images.

In step 803, a change to at least one feature of the projected pattern is detected in the received images, e.g. by the processing unit 13. In some embodiments performing step 803 comprises detecting a change to at least one feature of the projected pattern in the manner described above in relation to the operation of the processing unit 13. The result of step 803 may be a positive detection (i.e. it is detected that a change to at least one feature of the projected pattern has occurred) or a negative detection (i.e. it is detected that no changes have occurred to the at least one feature of the projected pattern). In some embodiments the output of step 803 comprises a result of a comparison between consecutive (in time) received images. In some such embodiments the result of the comparison comprises at least one change value, where each change value represents a measure of the change of a feature of the projected pattern. In some embodiments the result of the comparison comprises a set of change values, each corresponding to a different feature of the projected pattern. In some embodiments the output of step 803 comprises a change signal, e.g. based on a time-series of change values. In some embodiments the output of step 803 comprises a set of change signals, each corresponding to a different feature of the projected pattern.

In step 804, it is determined whether a detected change satisfies at least one predefined criterion for a subject exit event. In some embodiments performing step 803 comprises determining whether a detected change satisfies least one predefined criterion for a subject exit event in the manner described above in relation to the operation of the processing unit 13. In some embodiments step 804 is performed in response to the result of step 803 comprising a positive change detection. In some embodiments step 804 is performed continuously, e.g. each time a new change value is generated by step 803. In some embodiments the determination is performed based on change data (i.e. changes values or a change signal) covering a predefined time period, e.g. a time period leading up to the capture time of the most recently-received image, having a predefined length. The determination generated by step 804 may therefore be recalculated in respect of each newly-received image (or each subsequent frame of a video stream).

In step 805 a signal is output (e.g. by the processing unit 13) based on the determining (i.e. based on the result of step 804). In some embodiments performing step 805 comprises outputting a signal in the manner described above in relation to the operation of the processing unit 13. The signal may be output using a communications functionality of a monitoring device (e.g. the monitoring device 35). In some embodiments the signal is output continuously, in real-time or near-real time. In such embodiments, preferably the delay between the receipt of the images and the output of the signal is less than a few seconds, such that medical staff can respond rapidly to a detected bed exit event. In some embodiments the signal contains a result of a determination of whether a detected change satisfies at least one predefined criterion for a subject exit event (e.g. an indication that a subject exit event is likely to be occurring/have occurred, if the criterion is satisfied, or an indication that a subject exit event is not likely to be occurring/have occurred, if the criterion is not satisfied). In some embodiments the signal contains confidence information associated with the result of the determination generated in step 804. In some embodiments step 805 is only performed if the result of step 804 is that the at least one criterion is met. In some embodiments the signal contains time information associated with the result of the determination, e.g. the time period during which the detected change(s) on which the determination was based occurred. In some embodiments the signal contains information about a movement type. In some embodiments, e.g. embodiments in which a single camera is used to monitor multiple items of furniture, the signal contains information identifying an item of furniture with which a particular determination result is associated. In some embodiments performing step 805 comprises emitting multiple signals, each signal relating to a different monitored item of furniture.

In preferred embodiments the method of FIG. 8 is performed continuously during a time period, e.g. a time period for which the apparatus 10 is operational.

Embodiments of the invention therefore advantageously enable movements of a subject on an item of furniture to be automatically and unobtrusively monitored. Such monitoring can form the basis of a reliable and cost-effective system for detecting when a subject has, or is about to, exit an item of furniture.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. Apparatus for monitoring a subject, the apparatus comprising:
a projector fixedly attached to a moveable part of an item of furniture such that the projector, when attached to the moveable part, is located beneath a patient supporting surface of the item of furniture, wherein the moveable part is arranged to change its position and/or orientation relative to a surface in response to a movement of the subject occupying the item of furniture, and wherein the projector is arranged to project a first state of a pattern onto the surface;
at least one camera arranged to capture sequential images of the surface; and
a processing unit arranged to:
receive the images from the at least one camera;
detect the projected pattern in the received images,
detect a change to at least one feature of the projected pattern from the first state to a second state in the received images;
determine whether the detected change satisfies at least one predefined criterion for a subject exit event; and
output a signal based on the determining.

2. The apparatus of claim 1, further comprising an additional projector fixedly attached to the moveable part of the item of furniture, wherein the moveable part is arranged to change its position and/or orientation relative to a surface in response to the movement of a subject occupying the item of furniture, and wherein the additional projector is arranged to project a different pattern onto the surface.

3. The apparatus of claim 2,
wherein the projector and the additional projector are both fixedly attached to the same moveable part of the item of furniture, and wherein the projector is arranged to project onto a first region, and the additional projector is arranged to project onto a second region;
wherein the at least one camera is arranged to capture sequential images, each of which includes the first region and the second region.

4. The apparatus of claim 3, wherein the first region and the second region are located on opposite sides of the item of furniture.

5. The apparatus of claim 2,
wherein the projector is for attachment to a first item of furniture and is arranged to project a first pattern onto a first region, and the additional projector is for attachment to a second item of furniture and is arranged to project a second pattern onto a second region;
wherein the at least one camera is arranged to capture sequential images, each of which includes the first region and the second region; and
wherein the processing unit is arranged to:
detect the first projected pattern and the second projected pattern in the received images,
associate the first projected pattern with the first item of furniture and associate the second projected pattern with the second item of furniture;
detect a change to at least one feature of the first projected pattern and detect a change to at least one feature of the second projected pattern, in the received images;
determine whether the detected change to at least one feature of the first projected pattern satisfies at least one predefined criterion for a subject exit event and determine whether the detected change to at least one feature of the second projected pattern satisfies at least one predefined criterion for a subject exit event; and
output a signal based on the determining, wherein the output signal contains information identifying the first item of furniture and/or the second item of furniture.

6. The apparatus of claim 2,
wherein the projector is for attachment to an item of furniture at a first location, and the additional projector is for attachment to the same item of furniture at a second location, the second location being spatially separated from the first location;
wherein the projector is arranged to project onto a first region and the additional projector is arranged to project onto a second region; and
wherein the at least one camera is arranged to capture sequential images, each of which includes the first region and the second region.

7. The apparatus of claim 6, wherein the second region is the same as the first region, and wherein the projector is arranged to project a first partial pattern and the additional projector is arranged to project a second partial pattern such that a combined pattern comprising the first partial pattern and the second partial pattern is projected onto the first region.

8. The apparatus of claim 6, wherein the processing unit is arranged to detect a change to at least one feature of the projected pattern by:
detecting a first change associated with movement of the projector;
detecting a second change associated with movement of the additional projector; and
determining spatial information relating to a movement of a subject based on the detected first change and the detected second change.

9. The apparatus of claim 1, wherein the processing unit is arranged to detect a change to at least one feature of the projected pattern in the received images by:

comparing a first image, acquired at a first time, to a second image, acquired at a second, later, time, wherein the comparing comprises:

determining a first value relating to the at least one feature based on the first image;

determining a second value relating to the at least one feature based on the second image; and calculating a change value for the at least one feature, wherein the change value comprises the difference between the first determined value and the second determined value; and wherein the at least one predefined criterion comprises a minimum change value threshold.

10. The apparatus of claim 9, wherein the processing unit is arranged to detect a change to at least one feature of the projected pattern in the received images by generating a change signal, wherein the change signal is based on a time-series of calculated change values or on a time-series of determined first and/or second values, and wherein the at least one predefined criterion includes at least one condition relating to a feature of a change signal.

11. The apparatus of claim 1, wherein the at least one criterion comprises a predefined change signature corresponding to a movement type, and wherein the processing unit is arranged to determine whether the detected change satisfies the least one predefined criterion for the subject exit event by determining whether the detected change matches the change signature.

12. The apparatus of claim 1, wherein the projector is arranged to project near-infrared light and the camera is arranged to detect near-infrared light.

13. System for monitoring a subject occupying a bed, the system comprising:

a bed having a flexible bed base;

a projector disposed underneath the bed and fixedly attached to the flexible bed base, wherein the projector is arranged to project a pattern onto the floor;

a camera arranged to capture sequential images of the floor; and a processing unit arranged to:
  receive the images from the camera;
  detect the projected pattern in the received images,
  detect a change to at least one feature of the projected pattern in the received images;
  determine whether the detected change satisfies at least one predefined criterion for a subject bed exit event; and
  output a signal based on the determining.

14. Method for monitoring a subject occupying an item of furniture, the method comprising:

receiving sequential images of a surface, each of the images including a pattern projected onto the surface by a projector fixedly attached to a moveable part of an item of furniture, wherein the moveable part is arranged to change its position and/or orientation relative to the surface in response to a movement of the subject occupying the item of furniture, the images being received by a camera positioned such that the item of furniture is not within a field of view of the camera;

detecting the projected pattern in the received images, detecting a change to at least one feature of the projected pattern in the received images;

determining whether the detected change satisfies at least one predefined criterion for a subject exit event; and outputting a signal based on the determining.

15. The system of claim 13, wherein the processing unit is arranged to detect a change to at least one feature of the projected pattern in the received images by:

comparing a first image, acquired at a first time, to a second image, acquired at a second, later, time, wherein the comparing comprises:

determining a first value relating to the at least one feature based on the first image;

determining a second value relating to the at least one feature based on the second image; and calculating a change value for the at least one feature, wherein the change value comprises the difference between the first determined value and the second determined value; and wherein the at least one predefined criterion comprises a minimum change value threshold.

16. The system of claim 15, wherein the processing unit is arranged to detect a change to at least one feature of the projected pattern in the received images by generating a change signal, wherein the change signal is based on a time-series of calculated change values or on a time-series of determined first and/or second values, and wherein the at least one predefined criterion includes at least one condition relating to a feature of a change signal.

17. The system of claim 15, wherein the at least one criterion comprises a predefined change signature corresponding to a movement type, and wherein the processing unit is arranged to determine whether the detected change satisfies the least one predefined criterion for the subject bed exit event by determining whether the detected change matches the change signature.

18. The method of claim 14, wherein detecting a change to at least one feature of the projected pattern in the received images includes:

comparing a first image, acquired at a first time, to a second image, acquired at a second, later, time, wherein the comparing comprises:

determining a first value relating to the at least one feature based on the first image;

determining a second value relating to the at least one feature based on the second image; and calculating a change value for the at least one feature, wherein the change value comprises the difference between the first determined value and the second determined value; and wherein the at least one predefined criterion comprises a minimum change value threshold.

19. The method of claim 14, wherein the at least one criterion comprises a predefined change signature corresponding to a movement type, and wherein determining whether the detected change satisfies the least one predefined criterion for the subject exit event includes:

determining whether the detected change matches the change signature.

* * * * *